(12) United States Patent
Chen et al.

(10) Patent No.: US 9,333,236 B2
(45) Date of Patent: May 10, 2016

(54) METHOD OF TREATING LEUKEMIA USING RICE PROLAMIN

(71) Applicant: Mackay Memorial Hospital, Taipei (TW)

(72) Inventors: Yu-Jen Chen, Taipei (TW); Hui-Fen Liao, Chiayi (TW); Yu-Yawn Chen, Kaohsiung (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 75 days.

(21) Appl. No.: 14/530,545

(22) Filed: Oct. 31, 2014

(65) Prior Publication Data

US 2015/0051156 A1 Feb. 19, 2015

Related U.S. Application Data

(63) Continuation-in-part of application No. 12/845,039, filed on Jul. 28, 2010, now abandoned.

(30) Foreign Application Priority Data

Jan. 28, 2010 (TW) ............................... 99102483 A

(51) Int. Cl.
*A61K 38/00* (2006.01)
*A61K 38/16* (2006.01)

(52) U.S. Cl.
CPC ................................... *A61K 38/168* (2013.01)

(58) Field of Classification Search
CPC ....................................................... A61K 38/168
See application file for complete search history.

(56) References Cited

PUBLICATIONS

Chen et al., 2010, Prolamin, a rice protein, augments anti-leukaemia immune response, Journal of Cereal Science, 51: 189-197.*

* cited by examiner

*Primary Examiner* — Amber D Steele
(74) *Attorney, Agent, or Firm* — WPAT, P.C., Intellectual Property Attorneys; Anthony King

(57) ABSTRACT

The present invention relates to a method of treating leukemia using rice prolamin, comprising administering a daily dose of isolated prolamin to a patient suffering from leukemia for a period of time from 5 days to 10 days. For the treatment application, the rice prolamin can stimulate human peripheral blood mononuclear cell (PBMC) to produce cytokines, such as tumor necrosis factor-alpha, to inhibit growth of and induce differentiation of human leukemia cells. The rice prolamin is gluten-free, thus will not trigger gastrointestinal allergic reaction, it also can decrease the tumor weight without changes in body weight and can inhibit the growth of peripheral blood leukocyte in leukemia mouse model.

4 Claims, 7 Drawing Sheets

METHOD OF TREATING LEUKEMIA USING RICE PROLAMIN

CROSS REFERENCE TO RELATED APPLICATION

This application is a continuation-in-part of U.S. patent application Ser. No. 12/845,039, filed on Jul. 28, 2010, which is incorporated herewith by reference.

BACKGROUND OF THE INVENTION

1. Field of the Invention

The present invention relates to rice extracts for treating leukemia, especially relates to a rice prolamin that inhibits growth of leukemia cancer cells and induces differentiation of leukemia cancer cells through activating mononuclear cells.

2. The Prior Arts

Oryzae sativa (rice), one of the most important staple foods worldwide and the most commonly cultivated staple food in Taiwan, is rich in starch, protein (mainly the storage proteins), vitamins and minerals that provide essential nutrients to support human growth. In addition to its nutrition value, researches have shown that rice has many biological active ingredients. For example, flavonoids in rice can regulate cytochrome P450 activity (Noda, H., and Koizumi, Y. 2003. Sterol biosynthesis by symbiotes: cytochrome P450 sterol C-22 desaturase genes from yeastlike symbiotes of rice planthoppers and anobiid beetles. Insect Biochemistry & Molecular Biology. 33(6):649-58). Rice lipids contain anti-fungal active ingredients (Paranagama, P. A., Abeysekera, K. H., Abeywickrama, K., and Nugaliyadde, L. 2003. Fungicidal and anti-aflatoxigenic effects of the essential oil of *Cymbopogon citratus* (DC.) Stapf. (lemongrass) against *Aspergillus* flavus Link. isolated from stored rice. Letters in Applied Microbiology. 37(1):86-90). Rice bran can lower blood cholesterol (Qureshi, A. A., Sami, S. A. Salser, W. A., and Khan, E A. 2002. Dose-dependent suppression of serum cholesterol by tocotrienol-rich fraction (TRF25) of rice bran in hypercholesterolemic humans. Atherosclerosis. 161(1):199-207), enhance natural killer cell activity of aged mice (Ghoneum, M., and Abedi, S., 2004. Enhancement of natural killer cell activity of aged mice by modified arabinoxylan rice bran (MGN-3/Biobran). J. Pharm. Pharmacol. 56, 1581-1588), and induce apoptosis of human endometrial adenocarcinoma cells (Fan, H., Morioka, T., and Ito, E., 2000. Induction of apoptosis and growth inhibition of cultured human endometrial adenocarcinoma cells (Sawano) by an antitumor lipoprotein fraction of rice bran. Gynecol. Oncol. 76, 170-175).

Leukemia, also known as blood cancer, is the number one childhood cancer and up to 40% of childhood cancer is leukemia. Major causes of leukemia are related to lymphoid progenitor cells, affected by factors such as genetic inheritance, virus infection and medication, which become abnormally differentiated hematopoietic stem cells and lead to excess production of immature white blood cell in blood stream or bone marrow.

Although currently there have been great improvements in leukemia treatment, severe side effects and high recurrence rate are still the main difficulties to be overcome for complete treatment of the disease. Because of low curing rate of leukemia, development of novel effective therapeutics with small side effects remains an unmet medical issue.

SUMMARY OF THE INVENTION

To cure leukemia effectively and to minimize side effects during clinical application, an objective of the invention is to provide a method of treating leukemia comprising administering a rice prolamin to a human patient. A further objective of the invention is to provide a pharmaceutical composition for the treatment of leukemia comprising of an effective amount of rice prolamin together with one or more pharmaceutically acceptable carriers or excipients.

For the treatment method and the pharmaceutical composition described herein, the rice prolamin can stimulate human peripheral blood mononuclear cells (PBMC) to produce cytokines, such as tumor necrosis factors (TNF-$\alpha$), which can inhibit growth of leukemia cells or to stimulate differentiation of leukemia cells. In one embodiment of the present invention, the leukemia cell is U937 cell line. Furthermore, the rice prolamin of the invention is gluten-free.

In addition, rice prolamin of the present invention can decrease the tumor weight without changes in body weight, and can inhibit the growth of peripheral blood leukocyte in leukemia mouse model. Those results all indicate the anti-leukemic effect of rice prolamin not only in vitro but also in vivo.

Rice prolamin of the present invention can stimulate PBMCs and inhibit growth of human leukemia cells effectively, therefore, rice prolamin can be applied clinically to inhibit leukemia and used for preparation of pharmaceutical composition to treat leukemia. Because the rice prolamin is a natural ingredient that does not contain gluten (a protein that triggers intestinal allergy problems) and can induce differentiation of leukemia cells towards normal cells indirectly, thus, there is no concern of side effects when used in the treatment of leukemia.

The details of one or more embodiments of the invention are set forth in the description below. Other features, objects, and advantages of the invention will be apparent from the description and from the claims.

DETAILED DESCRIPTION OF THE PREFERRED EMBODIMENT

Figure 1:
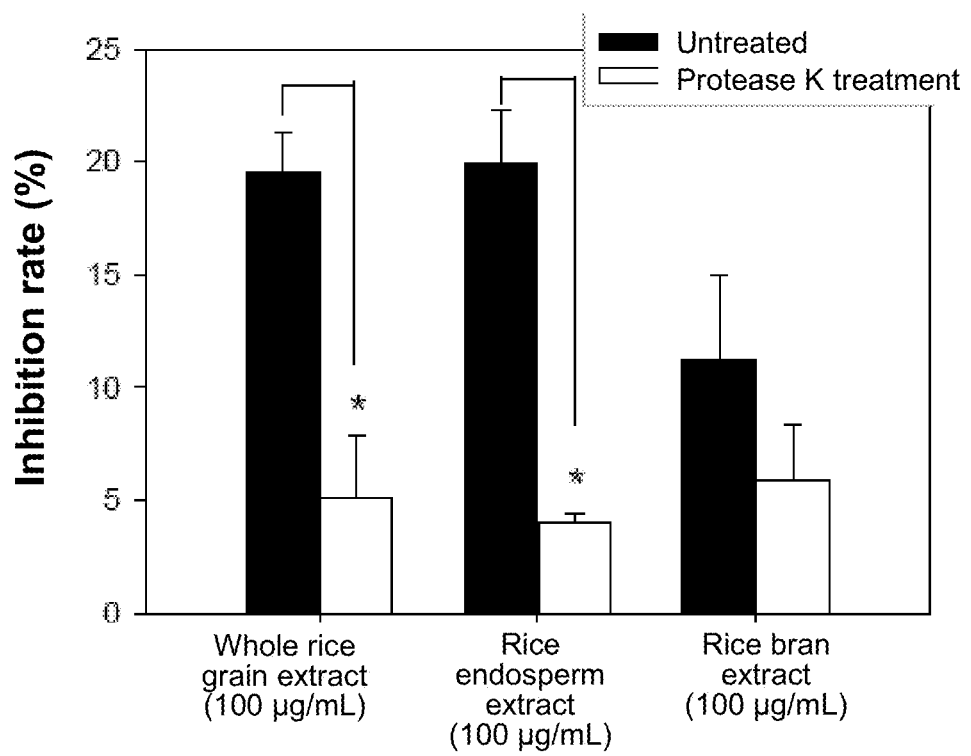
FIG. 1 showed indirect effect of whole rice grain, rice bran and endosperm extract, treated or untreated with protease K, on growth inhibition of leukemia U937 cells. Differences were considered significant at *$p<0.05$ when the experimental group was compared to the untreated control group.

To identify the biological active ingredient that has effect on inhibition of leukemia cell growth, one embodiment of the present invention first was to examine rice protein extracts that showed anti-cancer activity. The results indicated that rice protein extracts significantly inhibited growth of leukemia U937 cell line through stimulating cytokine secretion from PBMCs. Two dimensional gel electrophoresis and mass spectrometry were further applied to identify rice proteins that showed anti-tumor activity.

Because tumor cells are undifferentiated or immaturely differentiated cells, researches have shown that cancer cells can differentiate towards normal cells when treated with differentiation inducer, thus leading to low or no proliferation of cancer cells. Current studies suggest that some indirect immune stimulators, such as phytohemagglutinin, abbreviated as PHA below, can first stimulate immune cells to secrete large amount of cytokines which then induce leukemia cells to differentiate into mature and normal blood cells with functional activity. Such indirect immunity regulation by differentiation induction is a positive cancer treatment approach because of minimized side effects of chemotherapy or radiation therapy. However, PHA belongs to a type of mitogens, normally with certain toxicity. When PHA is applied clinically, certain concerns and problems do exist. Therefore, it is important to develop immune-stimulators without toxicity and no side effects.

Therefore, one embodiment of the invention was to use human peripheral blood mononuclear cells (PBMC) to test inhibitory activity of rice protein extracts on human leukemia U937 cell line by mechanism of immunity regulation, and to analyze immune response of tumor cells to rice protein extracts. The results of the invention showed that rice storage proteins could inhibit leukemia cell growth by regulating immunity of PBMC indirectly. Four storage proteins, including albumin, globulin, glutelin and prolamin isolated from rice by ddH$_2$O, salt, alkaline and ethanol extraction respectively, were tested for their biological activity. The results showed that one of the storage protein, prolamin, had highest anti-cancer activity. Test results also showed that the rice prolamin could activate and stimulate PBMC to secrete more cytokines and had significant inhibitory activity on leukemia U937 cells. The human monoblasic leukemia cell line U937 (obtained from the American Type Cuture Collection, ATCC, Rovkville, Md., USA) cells were cultured in RPMI 1640 medium (GIBCO, Grand Island, USA) containing 10% fetal calf serum and maintained in an exponential growth phase state.

On the other hand, isolation of PBMC and preparation of conditioned medium were described as below. Whole blood from healthy donator was placed in Ficoll-Hypaque solution (density at 1.077 g/ml, Pharmacia Fine Chemicals, USA) and centrifuged to separate PBMC. PBMC ($1.5 \times 10^6$ cells/mL) were incubated in RPMI 1640 medium supplemented with 10% heat-inactivated fetal calf serum (FCS, Hyclone, Logan, USA), and penicillin/streptomycin. Test materials such as rice extract could be added to the medium. After proper incubation, PBMC cells were removed and then supernatant was collected. These supernatants with test material were designated as peripheral blood mononuclear cell conditioned media (PBMC-CM) and used in growth inhibition test of leukemia U937 cells.

In addition, another invention was to demonstrate the anti-leukemic effect of rice prolamin by using isolated prolamin protein and a syngeneic leukemic mouse model.

Experiments of examples of the invention were all repeated at least three times, and the results were expressed as mean±standard error, variation among various groups was calculated as Student's t-test, and *p<0.05 indicated statistical significance.

EXAMPLE 1

Effect of Rice Protein Extracts on Leukemia

To identify which ingredient in the rice could inhibit the growth of leukemia cells, in this example, rice proteins were tested to examine their inhibitory activity on cancer cells.

Preparation of Rice Extracts

One example of the present invention was carried out using rice (*Oryza sativa*) grains of cultivars MT 9 (Japonica rice milled Taiwan 9, provided and by the Council of Agriculture, Executive Yuan, Taiwan). To prepare the rice extract, 1.0 g of MT 9 whole rice grain, rice bran and endosperm respectively, was grinded into powder and extracted by stirring with 50 ml of distilled boiled water for 30 min. Total rice extracts, rice bran extracts and endosperm extracts, respectively, were harvested by filtration.

One example of the present invention used whole grain, rice bran, and rice endosperm extract treated PBMC-CM, to investigate the effect of rice proteins on PBMC activation and their indirect anti-leukemia activity on leukemia U937 cells.

Extract of whole rice grain, rice bran and rice endosperm respectively, were treated with protease K (50 μg/mL) at 37° C. for 2 hrs and then boiled to inactivate protease activity (experimental group), and those untreated with protease were designated as control group. The experimental group and control group (at concentration of 100 μg/ml) were added to the RPMI 1640 medium that incubated with PBMC at 37° C. for 24 hr. The medium were filtered to remove PBMC, thus obtained the conditioned PBMC medium (PBMC-CM).

Human leukemia U937 cells (at density of $1 \times 10^5$/ml) were incubated in experimental group and control group of PBMC-CM, and PBMC-CM without extract supplementation was used as blank group. After 5 days of incubation at 37° C., cells grown at the bottom of the Petri-Dishes were collected by gently rubbing the dishes with a rubber policeman (Bellco Glass, Vineland, USA) and were used for the trypan blue dye exclusion test. The U937 cell suspension and trypan blue solution (diluted 10 fold with PBS solution before use) were properly mixed and number of viable and dead cells was counted under microscope with blood cell counter. Growth inhibition rate was calculated according to the following equation:

Growth inhibition ratio (%)=(1−viable cell number of experimental group or control group/viable cell number of blank group)×100%.

Trypan blue exclusion test is based on the principle that normal cells possessing intact cell membrane can exclude trypan blue dye, whereas the dye can permeating through damaged cell membrane of dead or damaged cells. The results were shown in FIG. 1.

An example of the present invention referred to FIG. 1. FIG. 1 showed indirect effect of whole rice grain, rice bran and endosperm extract (treated or untreated with protease K)

on growth inhibition of leukemia U937 cells. It was found that growth inhibition ratio of the control group (extracts untreated with protease K) on leukemia U937 cells was in the range of 10~20%; among which endosperm had highest inhibition activity. When these extracts were treated with protease K, growth inhibition activity reduced to barely 6% owing to degradation of rice proteins, that is, rice extracts without proteins had little effect on growth of leukemia U937 cells. The results indicated that the ingredients in the rice that inhibited leukemia U937 cells were proteins.

EXAMPLE 2

Analysis of Biologically Active Substances in Rice Protein

As shown in Example 1, the ingredients in the rice that possessing anti-leukemia activity were proteins, and inhibition activity of endosperm extract was superior to rice bran extract. Thus, the rice endosperm and rice bran extract of MT 9 were subjected to two dimensional gel electrophoresis and protein profile were compared. The invention further selected those unique protein spots that shown up at different position in two gels and analyzed them by mass spectrum, so that those specific proteins that inhibited leukemia U937 cell could be identified.

The two dimensional gel electrophoresis equipment used and the experimental protocol in one example of the invention were from Bio-Rad (Hercules, Calif.). Rice bran and endosperm of MT 9 reduced to powder were properly treated and quantified. Then, 50 mM dithiothreitol (DDT), 0.5% of readystrip IEF buffer (Bio-Lyte pH 3-10 and pH5-8 ampholyte Bio-Rad, CA) and rehydrated buffer were added to 25 μL of rice bran protein solution or 100 μL of endosperm solution to a final volume of 330 μL for isoelectrophoresis.

Figure 2A:
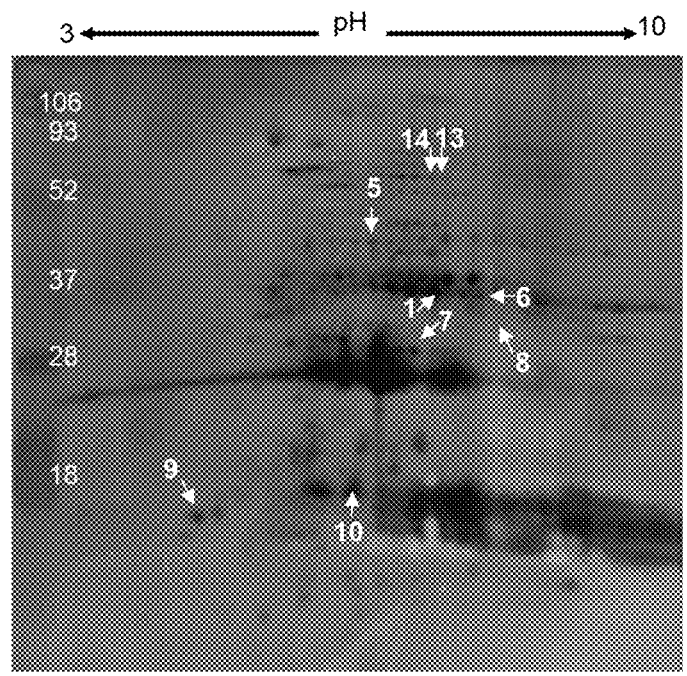
FIG. 2A was an example of two dimensional gel electrophoresis of MT 9 (Japonica rice milled Taiwan 9) rice endosperm. Arrows indicated the position of protein spots difference after analysis.
Figure 2B:
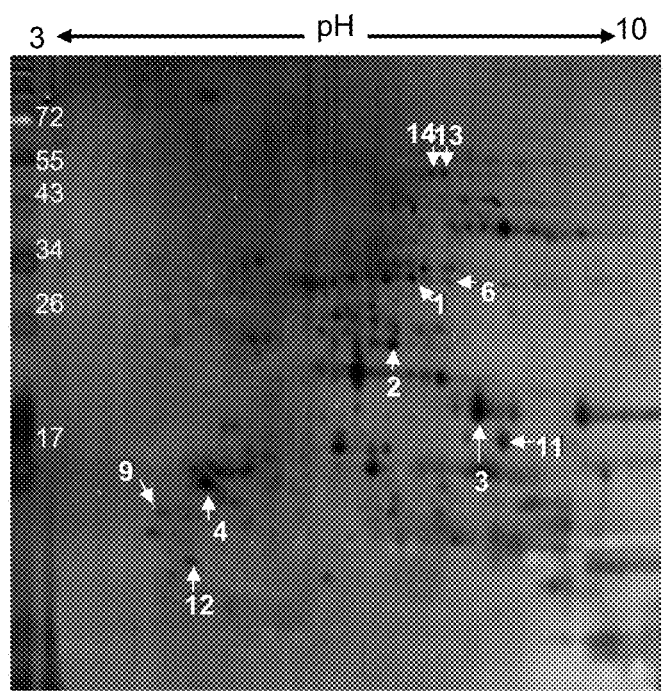
FIG. 2B was an example of two dimensional gel electrophoresis of MT 9 rice bran. Arrows indicated the position of protein spots difference after analysis.

After electrophoresis, visPRO 5 minutes protein stain kit for zinc stain was used to visualize protein spots. The results were shown in FIG. 2A and FIG. 2B.

Mass Spectrum Analysis of Rice Proteins

After staining, comparison of difference and quantification of rice bran protein spots and rice endosperm protein spots in two dimensional gel were analyzed using Image J (Version 1.38t, National Institutes of Health, Bethesda, Md.) software. For further Mass spectrometric identification of interesting protein spots, In-Gel protein digestion protocol was used for sample preparation, and followed by MALDI-QUAD-TOF analysis (Core Facilities for Proteomics and Structural Biology Research, Academia Sinica). Mass spectra data were submitted to database searches using the internet-based Mascot search tool to compare and molecular weight, pI and Score. The results were shown in Table 1.

Based on the results obtained from mass spectrometric and protein database analysis, those interesting proteins were identified and were further classified according to their biological function. Proteins with inhibitory activity against leukemia U937 cells were classified into 7 groups (as shown in Table 1), including (1) metabolism-related protein, such as dihydropteroate synthase (DHPS); (2) transport protein, such as response regulator receiver; (3) storage protein, such as glutelin; (4) antioxidant-related protein, such as 1-Cys peroxiredoxin A; (5) development protein, such as putative synovial sarcoma, X breakpoint 2 interacting protein; (6) disease resistance protein, such as NBS-LRR-like protein CR372; and unknown protein, such as hypothetical protein OsI_12089.

Shown in Table 1 were identified proteins, in which storage proteins (especially glutelin) shared the highest content, suggesting that storage proteins might play a role in inhibition of growth in leukemia U937 cells.

TABLE 1

Classification and identification od function proteins by MALDI-QUAD-TOF

| Classification | No. | Protein name | Accession number | pI | MW | Score | From | Endosperm/Bran (%) |
|---|---|---|---|---|---|---|---|---|
| Metabolism | 1-1 | Dihydropteroate synthase (DHPS) | 46906457 | 9.02 | 39454 | 91 | Bran | 229.84 |
|  | 3 | 3-phoshoshikimate 1-carboxyvinyltransferase | AROA_BACCR | 5.40 | 45287 | 72 | Bran | Bran only |
|  | 4-1 | Chemotaxis protein methyltransferase 2 | CHER2_VIBCH | 6.62 | 33610 | 50 | Bran | Bran only |
|  | 5 | Malate dehydrogenase, cytoplasmic | MDHC_BETVU | 5.89 | 35411 | 40 | Endosperm | Endosperm only |
|  | 9-1 | CoA-binding domain protein | 219668628 | 5.66 | 14597 | 56 | Endosperm | 150.64 |
| Transport | 7 | Response regulator receiver | 163849690 | 6.24 | 27367 | 54 | Endosperm | Endosperm only |
|  | 9-2 | Probable calcium-binding protein CML7 | CML7_ORYSJ | 4.89 | 16672 | 44 | Endosperm | 150.64 |
|  | 10-1 | Trigger factor | TIG_MAGSM | 4.68 | 49283 | 59 | Endosperm | Endosperm only |
|  | 14-1 | Guanine nucleotide-binding protein G(q) subunit alpha | GNAQ_HUMAN | 5.58 | 41441 | 43 | Bran | 59.84 |
| Storage | 1-2 | Glutelin | 31455453 | 6.60 | 35639 | 49 | Bran | 229.84 |
|  | 6-1 | Glutelin type I precursor | GLUA1_ORYSJ | 9.09 | 56212 | 108 | Endosperm | 118.60 |
|  | 6-2 | Glutelin precursor | A27033 | 9.17 | 56274 | 90 | Endosperm | 118.60 |
|  | 6-3 | Glutelin 2 precursor | B34332 | 9.17 | 56180 | 90 | Endosperm | 118.60 |
|  | 6-4 | Glutelin precursor | 225174 | 9.09 | 56196 | 108 | Endosperm | 118.60 |
|  | 6-5 | Glutelin II precursor | FWRZ2 | 8.93 | 56285 | 74 | Endosperm | 118.60 |
|  | 6-6 | Glutelin | 169791 | 9.17 | 56274 | 90 | Endosperm | 118.60 |
|  | 6-7 | Glutelin II precursor | A34332 | 8.93 | 56271 | 74 | Endosperm | 118.60 |
|  | 8 | Glutelin | 31455453 | 6.60 | 35639 | 64 | Endosperm | Endosperm only |
| Antioxidant | 2-1 | 1-Cys peroxiredoxin A | REHYA_ORYSJ | 5.97 | 24027 | 91 | Bran | Bran only |
|  | 2-2 | RAB24 protein | T03967 | 5.87 | 24127 | 76 | Bran | Bran only |
|  | 4-2 | Os07g0638300 | 115473617 | 5.97 | 24027 | 70 | Bran | Bran only |
|  | 11 | Ferredoxin-thioredoxin reductase catalytic chain, chloroplastic | FTRC_MAIZE | 8.61 | 16729 | 50 | Bran | Bran only |
|  | 13 | Putative oxidoreductase; putative 3-hydroxyisobutyrate dehydrogenase | 146337297 | 5.90 | 30720 | 55 | Bran | 57.45 |
| Development | 10-2 | Putative synovial sarcoma, X breakpoint 2 interacting protein | Q6Z0V1_ORYSA | 7.08 | 44567 | 61 | Endosperm | Endosperm only |
| Disease resistance | 12-1 | NBS-LRR-like protein CR372 | Q7Y063_ORYSA | 6.34 | 20782 | 59 | Bran | Bran only |
| Unknown | 12-2 | Hypothetical protein OsI_12089 | 218193065 | 5.32 | 20459 | 61 | Bran | Bran only |
|  | 12-4 | Hypothetical protein T08B1.4 | 193208661 | 6.95 | 38464 | 49 | Bran | 59.84 |

EXAMPLE 3

Assessment of Effect of Rice Storage Proteins on Leukemia

Although results of example 2 showed that the storage protein glutelin exhibited anti-leukemia U937 activity, rice contained high content of glutelin (for example, content of glutelin in endosperm is up to 80%). Therefore, it was possible that the great amount of glutein could mask the existence of relative scanty amounts of other storage proteins. Thus, storage proteins, including albumin, globulin, prolamin and glutelin were further analyzed for their individual anti-leukemia activity.

Extraction of Four Rice Storage Proteins

Extraction of four rice storage proteins of the invention was modified from Ju et. al. methods (Z. Y. Ju., N. S. Hettiarachchy, and N. Rath. 2001. Extraction, denaturation and hydrophobic Properties of Rice Flour Proteins. Journal of Food Science, 66(2):229-232.). The flow chart was shown in FIG. 3.

Rice endosperm (10 g) was grinded into powder with mortar and pestle and then defatted with 40 ml of Hexane for 24 hr. The defatted rice endosperm flour was then extracted by shaking with 40 ml of $ddH_2O$ at 20° C. for 4 hr and centrifuged at 3000 g for 30 min. Extraction was repeated twice in order to remove all the proteins. Supernatants thus obtained were mixed and designated as an albumin extract solution. After $ddH_2O$ extraction, the precipitate rice flour was extracted by shaking with 40 ml of 5% NaCl for 4 hr at 20° C. and centrifuged at 3000 g for 30 min. Extraction was repeated two times. Supernatants obtained were mixed and designated as a globulin extract solution. The flour was again extracted by shaking with 30 ml of 0.02M NaOH (adjusted to pH 11.0) at 20° C. for 4 hr and then centrifuged at 3000 g, 4° C. Extraction was repeated two times. Thus supernatants obtained were mixed and designated as a glutelin extract solution. After 0.02M NaOH extraction, the precipitates was extracted by shaking with 30 ml of 70% ethanol at 20° C. for 4 hr and then centrifuged at 3000 g for 30 min. This step was repeated two times. Supernatants obtained were mixed and designated as a prolamin extract solution. The prolamin extract solution was concentrated under reduced pressure at 40° C., 130 rpm to remove organic solvent. All these extracts were freeze dried at −50° C. and stored at 4° C. ready for use.

Assessment of Anti-leukemia Activity of Four Rice Storage Proteins

One example of the invention used the albumin extract solution, the globulin extract solution, the glutelin extract solution and the prolamin extract solution treated PBMC-CM, to investigate the effect of rice storage proteins on PBMC growth and their indirect anti-leukemia activity on leukemia U937 cells.

The albumin extracts, the globulin extract, the glutelin extract and the prolamin extract (the experimental groups, at concentration of 100 μg/ml), PBS, and DMSO (the control group), PHA (the positive control group, at concentration of 20 μg/ml), the rice endosperm extracts (at concentration of 100 μg/ml) as prepared according to Example 1 respectively, was added to the RPMI 1640 medium incubating with PBMC at 37° C. for 24 hr. The medium was filtered to remove PBMC, thus obtained the extract treated or test material (PBS, DMSO, PHA) treated PBMC-CM.

Human leukemia U937 cells (at density of $1 \times 10^5$/ml) were incubated in the albumin extract, the globulin extract, the glutelin extract and the prolamins extract (the experimental groups) treated PBMC-CM, PBS and DMSO (the control group) treated PBMC-CM, PHA (the positive group) treated PBMC-CM, endosperm extract (the reference group) treated PBMC-CM, and PBMC-CM without any additive (the blank group) respectively, at 37° C. for 5 days. After incubation, cells grown at the bottom of the Petri-Dishes were collected and used for the trypan blue dye exclusion test. The results of growth inhibition ratio under different PBMC-CM condition were calculated and shown in FIG. 4.

Figure 4:
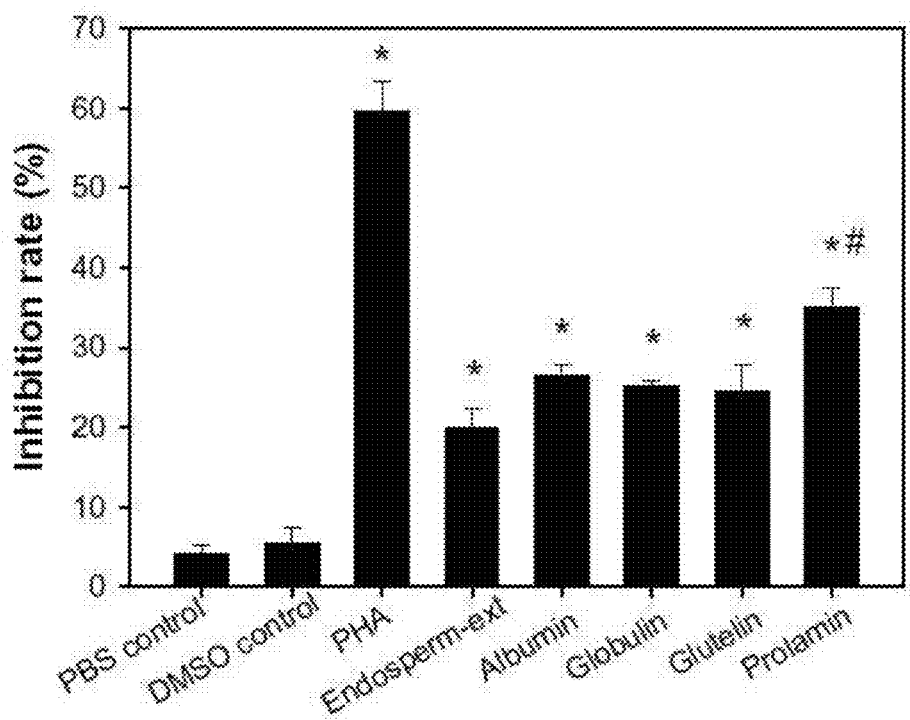
FIG. 4 showed indirect effect of four rice storage proteins on growth inhibition of leukemia U937 cells. Differences were considered significant at *$p<0.05$ when the experimental group was compared to the control group.

Referring to FIG. 4 there was the results of growth inhibition of four rice storage protein extracts on leukemia U937 cells via indirect anti-leukemia activity. In this Figure, it showed that growth inhibition ratio of rice albumin, globulin and glutelin extract on U937 was about 20-25%. On the other hand, growth inhibition of prolamin on leukemia U937 cells was up to 35%. Prolamin content in rice storage protein was the lowest (1 g of endosperm contains 11.8±2.9 mg prolamin, that is, prolamin content is only about 5-10% of all storage protein). Because the results showed that rice prolamin stimulated PBMC which then indirectly resulted in growth inhibition of U937 cells, suggesting that prolamin was the most active among the storage proteins and played an important role in inhibition of U937 cell growth.

In addition, observation of U937 cell morphology and differentiation cultivated in the presence of prolamin treated PBMC-CM (data not shown) showed that prolamin could induce U937 cells to differentiate into monocytes, thus driving the U937 cells towards normal cells and subsequently inhibiting tumor growth. On the other hand, cytokines (such as tumor necrosis factors, TNF-α) content in the prolamin treated PBMC-CM increased significantly (data not shown). Given that these cytokines could induce immune responses such as activation of B cell and T cell to facilitate tumor cell inhibition, these results suggested that prolamin could act as an important immuno-regulatory substance.

EXAMPLE 4

Effect of Rice Prolamin on Leukemia

Figure 5B:
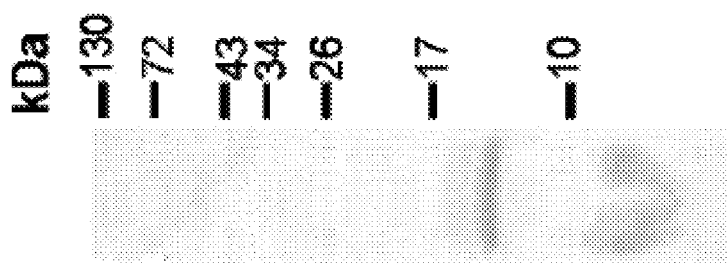
FIG. 5B exhibited SDS-PAGE analysis stained with coomassie blue of the anti-prolamin polyclonal antibody.
Figure 5A:
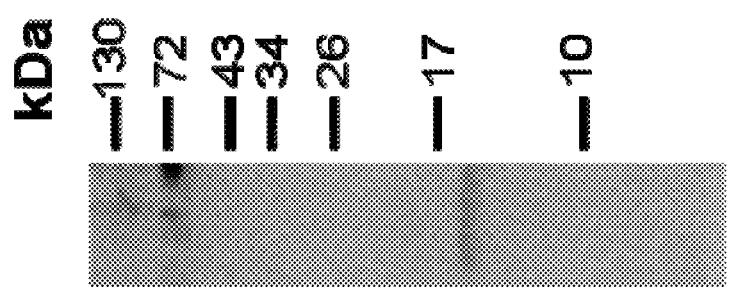
FIG. 5A exhibited the results of Western Blot of the anti-prolamin polyclonal antibody.

To further prove the role of prolamin on inhibition of leukemia, an example of the invention used a known method to prepare anti-prolamin polyclonal antibody. MT 9 endosperm was extracted with 70% ethanol to isolate prolamin. Freeze dried prolamin powder was re-solubilized and subjected to mini SDS-PAGE. Gel containing the prolamin protein band (the 15.5 kDa band) was cut off and then prolamin was properly eluted and collected. Prolamin (200 μg) was injected into rabbits (New Zealand white rabbits which diet do not contain rice). Rabbits were also received boost injection (at concentration of 100 μg anti-prolamin antibody) on week 2, 4 and 6. The full immunization course lasted for two and half month. The anti-prolamin polyclonal antibody was subjected to Western Blot (as shown in FIG. 5A) and SDS-PAGE stained with coomassie blue (as shown in FIG. 5B) for characterization.

Whole grain extract (500 μg/mL), endosperm extract (500 μg/mL), prolamin extract (100 μg/mL) was respectively neutralized with anti-prolamin polyclonal antibody (at dilution ratio of 1:1), and extracts un-neutralized with antibody were used as a control group. Human leukemia U937 cells were incubated in the PBMC-CM supplemented with these neutralized and un-neutralized solutions and growth inhibition of leukemia U937 cells were analyzed. The results were shown in FIG. 6.

Figure 6:
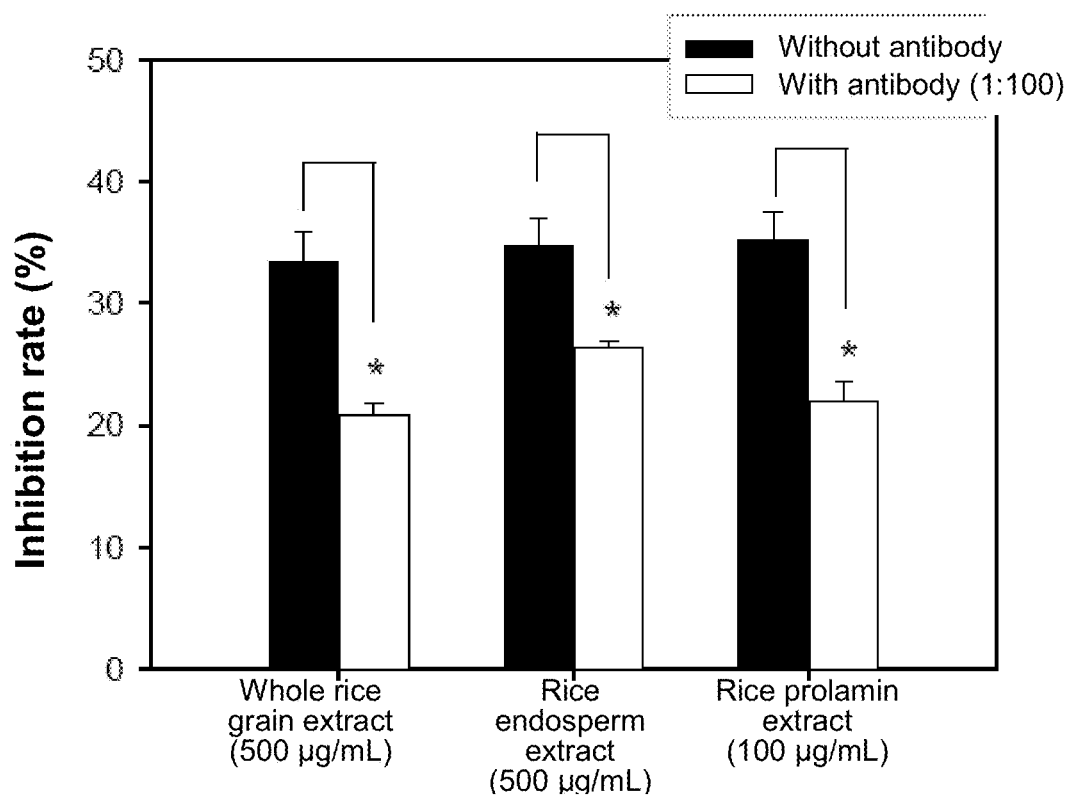
FIG. 6 showed the effect of whole rice grain extract, endosperm extract and prolamin extract neutralized with anti-prolamin antibody on growth inhibition of leukemia U937 cells. Differences were considered significant at *$p<0.05$ when the experimental group was compared to the control group.

Referring to FIG. 6 was an example of the invention shown the effect of whole rice grain extract, endosperm extract and prolamin extract neutralized with anti-prolamin antibody on growth of leukamin U937 cells. The results showed that the control group that without anti-prolamin polyclonal antibody neutralization had stronger inhibition on U937 cell growth, as compared to the experimental group with anti-prolamin antibody neutralization. It was believed that addition of anti-prolamin polyclonal antibody conjugated with prolamin in the extract, thus prolamin loss its biological activity. The results suggested that prolamin can stimulate PBMC and prolamin-treated PBMC-CM could inhibit U937 cell growth effectively. The results also proved that prolamin was the key ingredient responsible for anti-leukemia activity.

EXAMPLE 5

Confirmation of Rice Prolamin Does Not Cause Gastrointestinal Autoimmune Response Reports have shown that wheat gluten, containing gliadin and glutenin, and prolamin (derived from secalin, rye or barley), can trigger autoimmune response and induce autoimmune disease such as gluten sensitivity disease (GSD) or celiac disease (CD) (Fasano, A. and Catassi, C. 2001. Current approaches to diagnosis and treatment of celiac disease: an evolving spectrum. Gastroenterology, 120(3):636-651). Symptoms of these autoimmune diseases include persistent diarrhea, heart burn, excessive gas, and abdominal bloating. Currently there is no treatment for these diseases, and prevention of ingestion of these foods is the only approach to avoid these diseases. Therefore, the invention further analyzed if the rice prolamin contained gliadin peptide that may not trigger these autoimmune responses.

Gliadin, gluten, and a whole grain extract of Taikeng 9 and an endosperm extract of Taikeng 9, an albumin extract of Taikeng 9, a globulin extract of Taikeng 9, a glutelin extract of MT 9 and a prolamin extract of MT 9 were subject to Western blot and then hybridized with mouse anti-gliadin antibodies (Santa Cruz Biotechnology, Inc., Heidlberg Germany) (1:500 dilution). The results were shown in FIG. 7A and FIG. 7B.

Figure 7A:
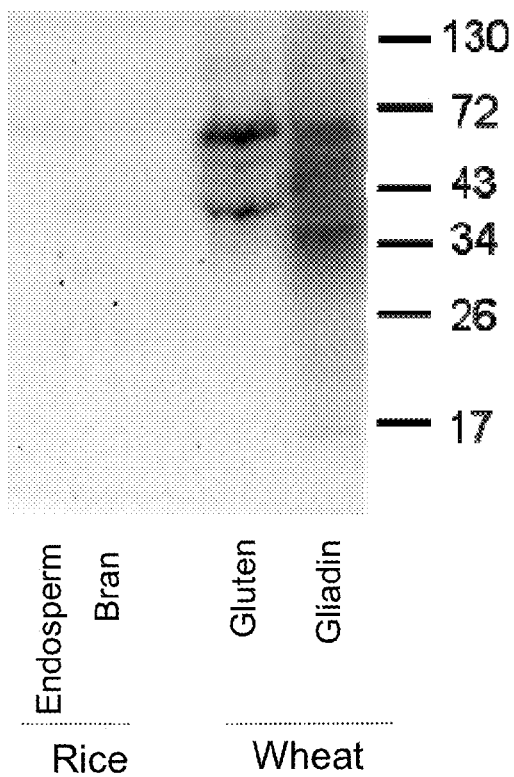
FIG. 7A illustrated the results of hybridization of the rice endosperm and the rice bran (Taikeng 9) with anti-gliadin antibodies respectively.
Figure 7B:
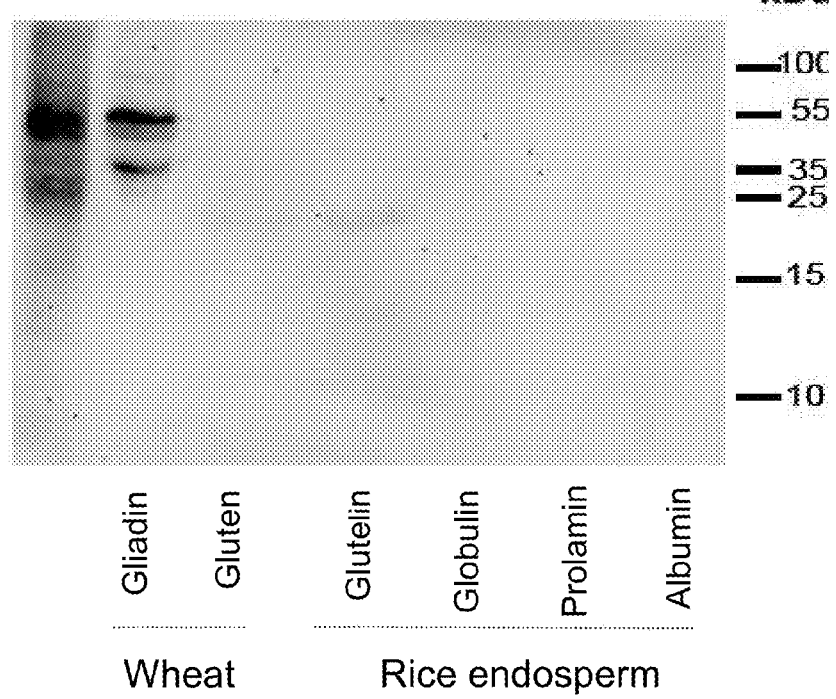
FIG. 7B illustrated the results of hybridization of four protein extracts (Taikeng 9) with anti-gliadin antibodies respectively.

An example of the invention referred to both FIG. 7A and FIG. 7B, in which FIG. 7A was the results of hybridization of endosperm and rice bran with anti-gliadin antibodies, and FIG. 7B was the results of hybridization of the albumin extract, the globulin extract, the glutelin extract and the prolamin extract with anti-gliadin antibodies. It was observed that gliadin was detected in wheat gliadin and gluten, whereas none of MT 9 rice endosperm, rice bran or extract of those four storage proteins was detected the presence of gliadin. The results indicated that these rice extracts did not contain gliadin that responsible for autoimmune diseases, so that ingestion of rice extract would not trigger autoimmune disease such as GSD or CD.

EXAMPLE 6

The Anti-Leukemic Effect of Rice Prolamin in Leukemia Mouse model

Figure 3:
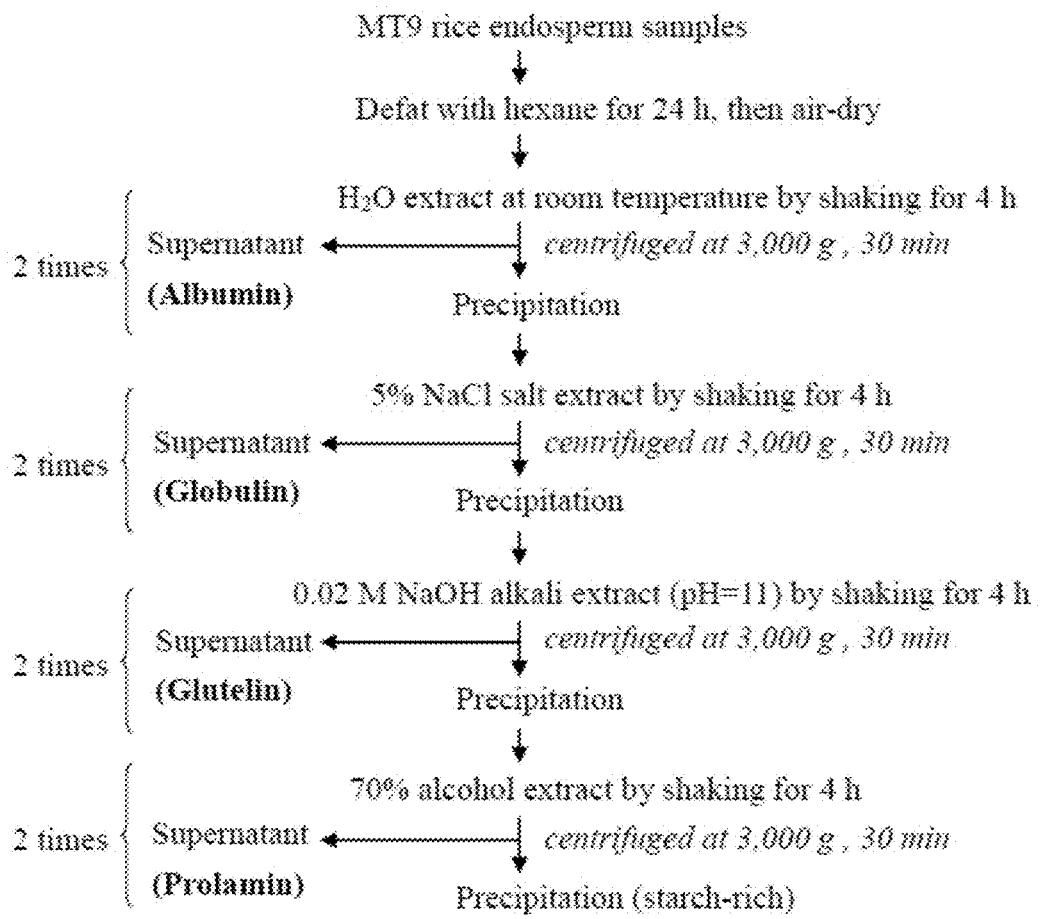
FIG. 3 illustrated the flow chart for extraction of four rice storage proteins: albumin, globulin, prolamin and glutelin.

To demonstrate the anti-leukemic effect of rice prolamin, we isolated the prolamin protein and used a syngeneic leukemic mouse model for validating the anti-leukemic effect of prolamin. And Rice protein prolamin was effectively extracted by using alcohol as solvent, as shown in FIG. 3.

Cell Culture and Animals

The DBA/2 mouse lymphocytic leukemia L1210 cell line (ATCC Number CCL-219) was obtained from Bioresource Collection and Research Center (BCRC), Taiwan. The L1210 cells was cultured in high glucose DMEM medium (Promocell, Heidelberg, Germany) supplemented with 15% certified FBS, 100 Unit/ml penicillin and 100 µg/ml streptomycin, and 0.1% mycoplasma removal agent at 37° C. in a humidified 5% $CO_2$ incubator. The DBA/2 mice (~7 weeks old, 18-22 g) were obtained from BioLASCO Taiwan Co., Ltd. All mice were housed in specific pathogen-free condition.

Syngeneic Mouse Model Assay

Syngeneic mouse model was used to evaluate the effect of prolamin on L1210 leukemia cells. L1210 cells ($1\times10^6$ cells per mouse) were injected into the mice through subcutaneous (s.c.) route. After 4 days, prolamin (diluted in normal saline) was administered by oral feeding (p.o.) every day for 5 days. All mice were divided into 4 groups with 6 animals for each group: (1) control group: normal mice which were treated with normal saline, (2) 0 mg/kg prolamin group: mice which were injected with L1210 cells by s.c., (3) 10 mg/kg prolamin group: prolamin 10 mg/kg p.o. per day in L1210-bearung mice, (4) 30 mg/kg prolamin group:prolamin 30 mg/kg p.o. per day in L1210-bearung mice. The body weight was recorded every day. Tumor weight, liver weight and spleen weight were recorded at sacrifice. Moreover, peripheral blood was collected for 5 days to record the leukocyte count in the blood.

The human equivalent dose of 0.8 mg prolamin/kg/day to 2.4 mg prolamin/kg/day is calculated by a previously published conversion method from mice dose of 10 mg prolamin/kg/day to 30 mg prolamin/kg/day, the conversion coefficient 12.3 is used to account for differences in body surface area between mice and humans.

Acute Toxicity of Prolamin on DBA/2 Mice

The toxicity was mainly assessed by body weight (BW) changes. No significant decrease in body weight was noted in prolamin-treated groups.

Weight of Tumor, Liver and Spleen in Syngeneic L1210-Bearing Mice

Comparing with the control group, prolamin decreased the tumor weight (16.3±2.3%, 11.2±1.5% and 9.6±1.9% of BW in 0 mg/kg prolamin group, 10 mg/kg prolamin group and 30 mg/kg prolamin group, respectively). The weight of liver and spleen of the mice was significantly decreased in 0 mg/kg prolamin group. Prolamin treatment inhibited the tumor-induced reduction in liver weight (6.3±0.6%, 3.7±1.0%, 3.9±1.6% and 4.6±1.1% of BW in control group, 0 mg/kg prolamin group, 10 mg/kg prolamin group and 30 mg/kg prolamin group, respectively) and spleen weight (0.52±0.12%, 0.24±0.09%, 0.31±0.14% and 0.31±0.13% of BW in control group, 0 mg/kg prolamin group, 10 mg/kg prolamin group and 30 mg/kg prolamin group, respectively) in L1210-bearing mice. Therefore, the results indicated the rice prolamin inhibited the tumor-induce reduction in liver and spleen weight and decreased the tumor weight.

Peripheral Blood Leukocyte Count

The peripheral blood leukocyte count was used to assess the anti-leukemia effect of prolamin on L1210 cells. The results show that the number of peripheral blood leukocyte significantly increased after L1210 cell inoculation. However, both dosages of prolamin (10 and 30 mg/kg for 5 consecutive days) significantly inhibited the increase of peripheral blood leukocyte count in the L1210-bearing mice. The peripheral blood leukocyte count was 1.3±0.1, 1.8±0.3, 1.6±0.4 and 1.5±0.2 ($\times10^7$/mL) in control group, 0 mg/kg prolamin group, 10 mg/kg prolamin group and 30 mg/kg prolamin group, respectively. The results indicated that rice prolamin significantly inhibited the increase of peripheral blood leukocyte.

In conclusion, rice proteins possessed anti-leukemia activity and inhibits growth of U937 cells. Two dimensional gel electrophoresis and mass spectrum analysis of these proteins indicate that they are metabolism, transport, storage, anti-oxidation, disease resistance, and proliferation related proteins. Further studies indicated that one of the storage protein, prolamin, could stimulate PBMC to secrete cytokines to inhibit the growth of and induce the differentiation of human leukemia cells. Furthermore, ingestion of prolamin would not trigger autoimmune diseases such as gluten sensitivity disease and celiac disease. Most important of all, the prolamin of the present invention can decrease the tumor weight without changes in body weight. And the prolamin inhibits the growth of peripheral blood leukocyte. Thus, the prolamin has an excellent anti-leukemia effect.

On the other hand, rice prolamin could be prepared as pharmaceutical composition to treat leukemia. In addition to the rice prolamin at an effective concentration, the pharmaceutical composition could also contain the following pharmacologically acceptable carriers but is not limited thereto: excipients include liquids (such as water), fillers (such as sucrose or starch), binders (such as cellulose derivatives), diluents, disintegrant, absorption enhancers or sweeteners. The present invention of the pharmaceutical composition can also be prepared by known methods of pharmaceutical production, mixing the effective amount of rice prolamin with any of carriers described above and produced in any possible dosage form including but not limited to tablets, powder, capsule or liquid form.

What is claimed is:

1. A method of treating leukemia comprises:
   administering a daily dose of an isolated prolamin to a patient suffering from leukemia for a period of time from 5 days to 10 days,
   wherein the daily dose comprises 0.8 mg prolamin/kg to 2.4 mg prolamin/kg, and the isolated prolamin is derived from rice.

2. The method of claim 1, wherein the isolated prolamin stimulates human peripheral blood mononuclear cells (PBMC) to produce a cytokine, which further induces differentiation of leukemia cells.

3. The method of claim 2, wherein the cytokine is a tumor necrosis factor (TNF-$\alpha$).

4. The method of claim 1, wherein the isolated prolamin is administered by oral feeding.

* * * * *